United States Patent
Carr et al.

[11] 3,941,795
[45] *Mar. 2, 1976

[54] α-ARYL-4-SUBSTITUTED PIPERIDINOALKANOL DERIVATIVES

[75] Inventors: Albert A. Carr; C. Richard Kinsolving, both of Cincinnati, Ohio

[73] Assignee: Richardson-Merrell Inc., Wilton, Conn.

[ * ] Notice: The portion of the term of this patent subsequent to Apr. 15, 1992, has been disclaimed.

[22] Filed: Feb. 8, 1974

[21] Appl. No.: 440,855

[52] U.S. Cl. 260/293.83; 260/247.5 G; 260/268 H; 260/293.62; 260/293.64; 260/293.68; 260/293.71; 260/293.79; 260/293.84; 424/248; 424/250; 424/267
[51] Int. Cl.² .................................. C07D 211/22
[58] Field of Search..... 260/293.64, 293.68, 293.79, 260/293.83, 293.84, 293.62, 293.71, 247.5 G, 268 H

[56] References Cited
UNITED STATES PATENTS

| | | | |
|---|---|---|---|
| 3,806,526 | 4/1974 | Carr et al. | 260/293.64 |
| 3,829,433 | 8/1974 | Carr et al. | 260/293.79 |
| 3,839,431 | 10/1974 | Sheehan et al. | 260/515 R |

FOREIGN PATENTS OR APPLICATIONS 794,597  5/1973  Belgium

Primary Examiner—G. Thomas Todd
Attorney, Agent, or Firm—L. Ruth Hattan; Eugene O. Retter; George W. Rauchfuss, Jr.

[57] ABSTRACT

Novel compounds useful as antihistamine agents, antiallergy agents, and bronchodilators are represented by the following formula

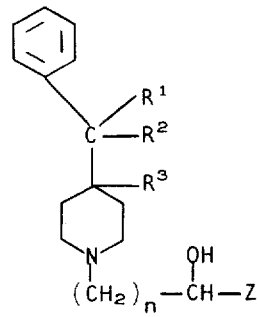

wherein $R^1$ represents cyclohexyl, phenyl, or substituted phenyl wherein the substituent on the substituted phenyl is selected from halogen, a straight or branched lower alkyl group of from 1 to 4 carbon atoms, or a lower alkoxy group of from 1 to 4 carbon atoms; $R^2$ represents hydrogen or hydroxy; $R^3$ represents hydrogen, or $R^2$ and $R^3$ taken together form a second bond between the carbon atoms bearing $R^2$ and $R^3$; n is an integer of from 1 to 3; Z represents thienyl, naphthyl, phenyl, or substituted phenyl wherein the substituent on the substituted phenyl may be attached at the ortho, meta or para position of the phenyl ring and is selected from halogen, a straight or branched alkyl group of from 1 to 6 carbon atoms, an alkoxy group of from 1 to 6 carbon atoms, a cycloalkyl group of from 3 to 6 carbon atoms, di(lower)alkylamino, or a saturated monocyclic heterocyclic group such as pyrrolidino, piperidino, morpholino, or N-(lower)-alkylpiperazino with the proviso that when $R^1$ is phenyl, Z is naphthyl or phenyl substituted with a straight or branched alkyl group of 5 or 6 carbon atoms, a lower alkoxy group of 5 or 6 carbon atoms, or a cycloalkyl group of from 3 to 6 carbon atoms. Pharmaceutically acceptable acid addition salts and individual optical and geometric isomers of compounds of the above formula are also included as a part of this invention.

7 Claims, No Drawings

α-ARYL-4-SUBSTITUTED PIPERIDINOALKANOL DERIVATIVES

FIELD OF THE INVENTION

This invention relates to novel substituted piperidine derivatives which are useful as antihistamine agents, antiallergy agents and bronchodilators and to methods of making and using the same.

BACKGROUND OF THE INVENTION

Belgium patent No. 794,597 which is equivalent to U.S. Application Ser. No. 378,561 now U.S. Pat. No. 3,878,217 which is a continuation-in-part of U.S. application Ser. No. 221,821, now abandoned describes compounds useful as antihistamine agents, antiallergy agents and bronchodilators having the formula

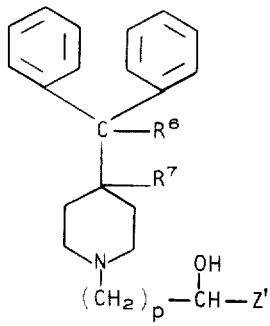

wherein $R^6$ represents hydrogen or hydroxy; $R^7$ represents hydrogen; or $R^6$ and $R^7$ taken together form a second bond between the carbon atoms bearing $R^6$ and $R^7$; p is a positive whole integer of from 1 to 3; Z' represents thienyl, phenyl, or substituted phenyl wherein the substituents on the substituted phenyl may be attached at the ortho, meta, or para positions of the phenyl ring and are selected from halogen, a straight or branched lower alkyl chain of from 1 to 4 carbon atoms, a lower alkoxy group of from 1 to 4 carbon atoms, di(lower)alkylamino, or a saturated monocyclic heterocyclic group such as pyrrolidino, piperidino, morpholino, or N-(lower)alkylpiperazino. Pharmaceutically acceptable acid addition salts and individual optical isomers of compounds of the above formula are also disclosed.

SUMMARY OF INVENTION

The novel substituted piperidine derivatives of this invention are useful as antihistamine agents, antiallergy agents and bronchodilators and are represented by the formula

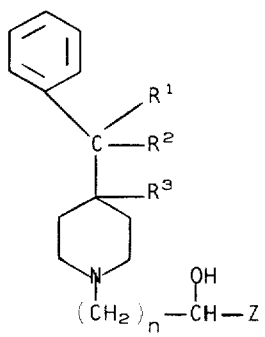

Formula I wherein $R^1$ represents cyclohexyl, phenyl, or a substituted phenyl ring wherein the substituent on the substituted phenyl ring is attached at the ortho, meta or para position of the phenyl ring and is selected from halogen, a straight or branched lower alkyl group of from 1 to 4 carbon atoms, or a lower alkoxy group of from 1 to 4 carbon atoms; $R^2$ represents hydrogen or hydroxy; $R^3$ represents hydrogen; or $R^2$ and $R^3$ taken together form a second bond between the carbon atoms bearing $R^2$ and $R^3$; n is an integer of from 1 to 3; Z represents thienyl, naphthyl, phenyl, or a substituted phenyl ring wherein the substituent on the substituted phenyl ring is attached at the ortho, meta or para position of the phenyl ring and is selected from halogen, a straight or branched alkyl group of from 1 to 6 carbon atoms, an alkoxy group of from 1 to 6 carbon atoms, a cycloalkyl group of from 3 to 6 carbon atoms, di(lower)alkylamino, or a saturated monocyclic heterocyclic group such as pyrrolidino, piperidino, morpholino or N-(lower)alkylpiperazino with the proviso that when $R^1$ is phenyl, Z is naphthyl or a substituted phenyl ring wherein the substituent on the substituted phenyl ring is attached at the ortho, meta or para position of the phenyl ring and is selected from a straight or branched alkyl group of 5 or 6 carbon atoms, an alkoxy group of 5 or 6 carbon atoms, or a cycloalkyl group of from 3 to 6 carbon atoms. Pharmaceutically acceptable acid addition salts and individual optical and geometric isomers of the compounds of Formula I are included in the scope of this invention.

DETAILED DESCRIPTION OF INVENTION

The compounds of this invention are 4-(disubstitutedmethyl)piperidine derivatives, 4-(disubstitutedmethanol)piperidine derivatives, or 4-(disubstitutedmethylene)piperidine derivatives as represented by the following respective Formulas II to IV

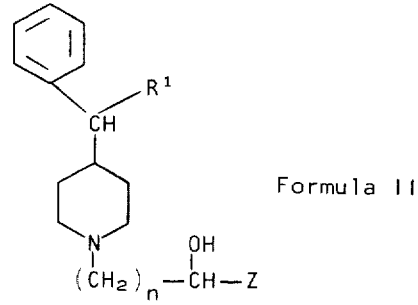

Formula II

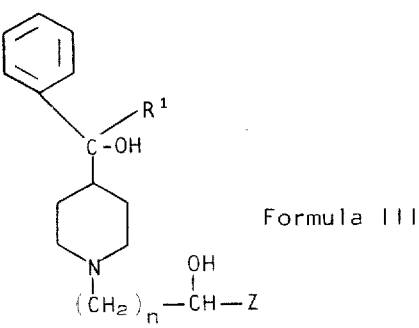

Formula III

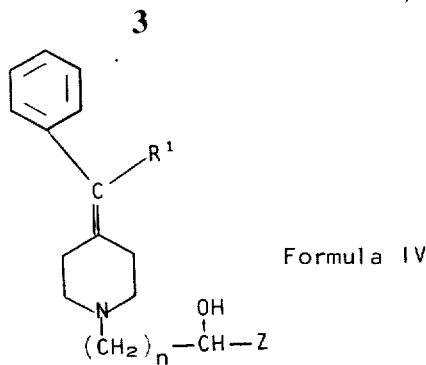

Formula IV

In the above Formulas II, III and IV, $R^1$, $n$, and Z have the meanings described in Formula I.

The term halogen as used herein is taken to mean bromine, chlorine, fluorine or iodine. Preferred halogens are chlorine and fluorine.

Illustrative examples of straight or branched lower alkyl groups of from 1 to 4 carbon atoms that may be present as the substituent on the substituted phenyl as represented by $R^1$ in Formulas I to IV are methyl, ethyl, n-propyl, isopropyl, n-butyl, and tert-butyl.

Illustrative examples of lower alkoxy groups of from 1 to 4 carbon atoms that may be present as the substituent on the substituted phenyl as represented by $R^1$ in Formulas I to IV are methoxy, ethoxy, propoxy and butoxy. Illustrative examples of alkoxy groups of from 1 to 6 carbon atoms that may be present as the substituent on the substituted phenyl as represented by Z in Formulas I to IV are methoxy, ethoxy, propoxy, butoxy, pentoxy, and hexyloxy.

Illustrative examples of straight or branched alkyl groups of from 1 to 6 carbon atoms that may be present as the substituent on the substituted phenyl as represented by Z in Formulas I to IV are methyl, ethyl, n-propyl, isopropyl, isobutyl, tert-butyl, n-butyl, n-pentyl, neopentyl, and n-hexyl. The term cycloalkyl as used herein represents cyclopropyl, cyclobutyl, cyclopentyl and cyclohexyl.

The term (lower)alkyl as used in describing the groups di(lower)alkylamino and N-(lower)alkylpiperazino each of which may be the substituent on the substituted phenyl as represented by Z in Formulas I to IV is taken to mean a straight or branched lower alkyl group of from 1 to 4 carbon atoms illustrative examples of which are methyl, ethyl, n-propyl, isopropyl, n-butyl and tert-butyl.

When in Formulas I to IV $R^1$ represents a phenyl group, Z represents naphthyl or a substituted phenyl wherein the substituent on the substituted phenyl may be attached at the ortho, meta or para position of the phenyl ring and is selected from a straight or branched alkyl group of 5 to 6 carbon atoms, an alkoxy group of 5 to 6 carbon atoms, or a cycloalkyl group of 3 to 6 carbon atoms and may be represented by the following Formula V:

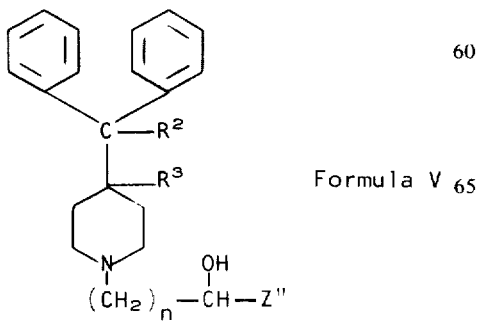

Formula V wherein $R^2$, $R^3$ and n have the meanings defined in Formula I, and Z'' represents naphthyl or a substituted phenyl ring wherein the substituent on the substituted phenyl ring is selected from a straight or branched alkyl group of 5 or 6 carbon atoms, an alkoxy group of 5 or 6 carbon atoms or a cycloalkyl group of from 3 to 6 carbon atoms and wherein said substituent may be attached at the ortho, meta or para position of the phenyl ring.

The compounds of this invention as represented by Formulas I to IV wherein $R^1$ represents cyclohexyl or substituted phenyl may be further illustrated by the following respective Formulas VI and VII.

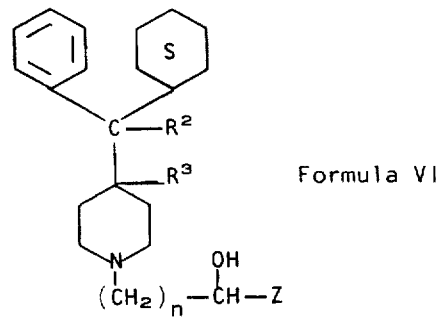

Formula VI

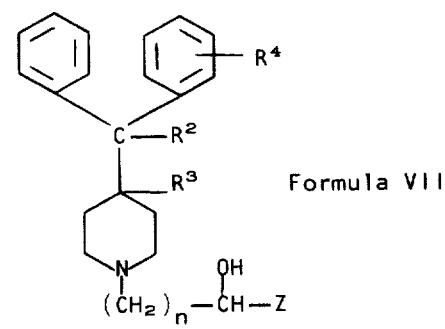

Formula VII

In the above Formulas VI and VII $R^2$, $R^3$, $n$ and Z have the meanings defined in Formula I, and $R^4$ represents halogen, a straight or branched lower alkyl group of from 1 to 4 carbon atoms or a lower alkoxy group of from 1 to 4 carbon atoms.

Preferred compounds of this invention are those wherein Z is other than naphthyl or thienyl. More preferred compounds of this invention are those wherein Z is other than thienyl or naphthyl, and n is equal to 3.

This invention also includes the pharmaceutically acceptable acid addition salts of the compounds of the hereinbefore set forth formulas, optical and geometric isomers and salts thereof. Pharmaceutically acceptable acid addition salts of the compounds of this invention are those of any suitable inorganic or organic acid. Suitable inorganic acids are, for example, hydrochloric, hydrobromic, sulphuric, and phosphoric acids. Suitable organic acids include carboxylic acids such as, for example, acetic, propionic, glycolic, lactic, pyruvic, malonic, succinic, fumaric, malic, tartaric, citric, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acid and the like, sulfonic acids such as, for example, methanesulfonic, ethanesulfonic, and β-hydroxyethanesulfonic acid.

Illustrative examples of compounds of this invention are α-(p-fluorophenyl)-4-[α-hydroxy-α-(p-chlorophenyl)benzyl]-1-piperidinebutanol, 4-[α-hydroxy-α-(m-propoxyphenyl)benzyl]-α-phenyl-1-piperidinebutanol, 4-[α-hydroxy-α-(o-anisyl)benzyl]-α-(p-pentylphenyl)-1-piperidinebutanol, α-(p-tert-butylphenyl)-4-[α-(p-tolyl)benzyl]-1-piperidinepropanol, 4-[α-(p-tert-butylphenyl)benzylidene]-α-(p-dimethylaminophenyl)-1-piperidinebutanol, 4-[α-(p-fluorophenyl)benzyl]-α-(p-morpholinophenyl)-1-piperidineethanol, α-(m-ethoxyphenyl)-4-[α-(p-ethylphenyl)benzyl]-1-piperidinepropanol, 4-[α-(p-methoxyphenyl)benzyl]-α-(2-thienyl)-1-piperidinebutanol, 4-(α-hydroxy-α-cyclohexylbenzyl)-α-[p-(N-methylpiperazino)phenyl]-1-piperidinebutanol, 4-(α-cyclohexylbenzylidene)-α-(p-methoxyphenyl)-1-piperidinebutanol, 4-(α-hydroxy-α-phenylbenzyl)-α-(p-neopentylphenyl)-1-piperidinebutanol, α-(p-cyclopropylphenyl)-4-(α-hydroxy-α-phenylbenzyl)-1-piperidinepropanol, α-(p-cyclopentylphenyl)-4-(α,α-diphenylmethyl)-1-piperidineethanol, 4-[α-(p-n-butoxyphenyl)benzyl]-α-(p-cyclohexylphenyl)-1-piperidinebutanol, 4-(α,α-diphenylmethylene)-α-(p-hexyloxyphenyl)-1-piperidinebutanol, 4-(α,α-diphenylmethylene)-α-(2-naphthyl)-1-piperidinepropanol, and 4-[α-(m-n-pentoxyphenyl)benzylidene]-α-(o-hexylphenyl)-1-piperidinebutanol.

The novel compounds of this invention are useful as antihistamines, antiallergy agents and bronchodilators and may be administered alone or with suitable pharmaceutical carriers to warm blooded animals, mammals, such as felines, canines, bovine, porcine, equine and humans, and can be in solid or liquid form such as, for example, tablets, capsules, powders, solutions, suspensions, or emulsions. The compounds of this invention can be administered orally, parenterally, for example, subcutaneously, intravenously, intramuscularly, intraperitoneally, by intranasal instillation or by application to mucous membranes such as that of the nose, throat, and bronchial tubes, for example, in an aerosol spray containing small particles of a compound of this invention in a spray or dry powder form.

The quantity of novel compounds administered will vary. Depending on the patient and the mode of administration, the quantity of novel compound administered may vary over a wide range to provide in a unit dosage of from about 0.01 to 20 milligrams per kilogram of body weight of the patient per dose to achieve the desired effect. For example the desired antihistamine, antiallergy and bronchodilator effects can be obtained by consumption of a unit dosage form such as, for example, a tablet containing 1 to 100 milligrams of a novel compound of this invention taken 1 to 4 times daily.

The solid unit dosage forms can be of the conventional type. Thus, the solid form can be a capsule which can be of the ordinary gelatin type containing a novel compound of this invention and a carrier, for example, lubricant and inert fillers such as lactose, sucrose, corn starch, and the like. In another embodiment, the novel compounds are tabletted with conventional tablet bases such as lactose, sucrose, corn starch, and the like in combination with binders such as acacia, corn starch or gelatin, disintegrating agents such as corn starch, potato starch, or alginic acid, and a lubricant such as stearic acid, or magnesium stearate.

The novel compounds may also be administered as injectable dosages by solution or suspension of the compounds in a physiologically acceptable diluent with a pharmaceutical carrier which can be a sterile liquid such as water and/or oils, with or without the addition of a surfactant and other pharmaceutically acceptable adjuvants. Illustrative of oils there can be mentioned those of petroleum, animal, vegetable or synthetic origin, for example, peanut oil, soybean oil, mineral oil, and the like. Water, saline, aqueous dextrose, and related sugar solutions, ethanols and glycols such as propylene glycol or polyethylene glycol are illustrative of liquid carriers for injectable solutions.

For use as aerosols the novel compounds in solution or suspension may be packaged in a pressurized aerosol container together with a gaseous or liquefied propellant, for example, dichlorodifluoromethane, dichlorodifluoromethane with dichlorodifluoroethane, carbon dioxide, nitrogen, propane, etc. with the usual adjuvants such as co-solvents, and wetting agents, as may be necessary or desirable. The compounds may also be administered in a non-pressurized form such as in a nebulizer or atomizer.

To illustrate the utility of the compounds of this invention the following tabulation indicates the amount of certain representative compounds of this invention required to reduce by 50% wheals induced by intradermal injections on 1γ of histamine into guinea pigs. Each compound was orally administered one hour prior to the histamine injection.

| Compound | $ED_{50}$, mg/kg |
| --- | --- |
| 4-(α-cyclohexyl-α-hydroxybenzyl)-α-(p-tert-butylphenyl)-1-piperidinebutanol hydrochloride | 12.0 |
| α-(p-tert-butylphenyl)-4-[α-(o-anisyl)benzylidene]-1-piperidinebutanol | 4.4 |

The compounds of this invention may be prepared by reducing the corresponding aryl 4-substituted piperidinoalkyl ketone as illustrated by the following:

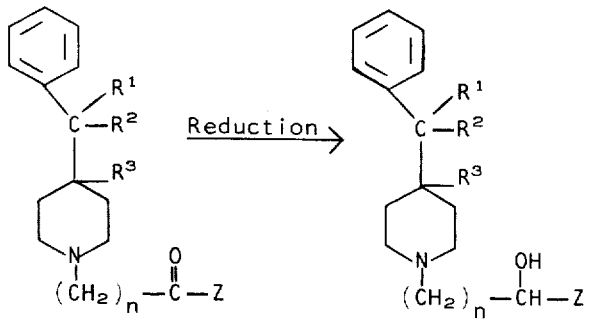

Formula I

In the above reaction $R^1$, $R^2$, $R^3$, n, and Z have the meanings defined in Formula I.

Preferred reducing agents such as sodium borohydride may be employed in the above reaction using a lower alcohol solvent such as methanol, isopropyl alcohol, tertbutanol and the like. The reaction is carried out at temperatures ranging from about 0°C to the reflux temperature of the solvent, and the reaction time varies from about 0.5 to about 8 hours. Other hydrides as reducing agents such as lithium aluminum hydride and diborane may also be used in an appropriate solvent such as diethyl ether.

This reaction may also be achieved by catalytic reduction using Raney nickel, palladium, platinum or rhodium catalysts in lower alcohol solvents, acetic acid, or their aqueous mixtures, or by aluminum isopropoxide in isopropanol.

The aryl substituted piperidinoalkyl ketones as represented by compound 1 may be prepared by an alkylation reaction of an appropriately substituted piperidine derivative with an ω-haloalkyl aryl ketone derivative in alcoholic solvents such as methanol, ethanol, isopropyl alcohol, n-butanol, in ketone solvents such as n-butanone, and methyl isobutyl ketone, in hydrocarbon solvents such as benzene, and toluene, or in halogentaed hydrocarbons, such as chlorobenzene, and the like, in the presence of an inorganic base such as sodium bicarbonate, or potassium carbonate or in the presence of an organic base such as triethylamine, or an excess of compound 1. In some cases it may be desirable to add catalytic amounts of potassium iodide to the reaction mixture. The reaction time is usually about 48 hours, but may vary from about 4 to 120 hours at a temperature of from about 70°C to the reflux temperature of the solvent.

The compounds of this invention may also be prepared by the alkylation of 4-diphenylmethylenepiperidine, 4-diphenylmethylpiperidine, or α,α-diphenyl-4-piperidinemethanol with an α-aryl-ω-haloalkanol derivative in an alcoholic or a hydrocarbon solvent in the presence of a base for from about 24 to 72 hours at a temperature varying from about 70°C to the reflux temperature of the solvent.

The following examples are illustrative of the invention.

EXAMPLE 1

4-[α-(p-tert-Butylphenyl)-α-hydroxybenzyl]-α-phenyl-1-piperidinebutanol

To a mixture of 4.2 g (0.0083 mole) of 4-[4-[α-(p-tert-butylphenyl)-α-hydroxybenzyl]piperidino]-butyrophenone hydrochloride and 0.54 g (0.01 mole) of sodium methoxide in 25 ml of methanol is added 2.16 g (0.04 mole) of potassium borohydride. The reaction mixture is stirred overnight, diluted with water and the methanol removed under reduced pressure. The remaining material is extracted with chloroform, washed with water, dried over magnesium sulfate and filtered. The filtrate is concentrated, and the residue is recrystallized from acetone-water to give 4-[α-(p-tert-butylphenyl)-α-hydroxybenzyl]-α-phenyl-1-piperidinebutanol, M.P. 161°–163°C.

EXAMPLE 2

α-(4-tert-Butylphenyl)-4-(α-cyclohexyl-α-hydroxybenzyl) 1-piperidinebutanol

When in the procedure of Example 1 an appropriate amount of 4-[4-(α-cyclohexyl-α-hydroxybenzyl)-piperidino]4'-tert-butylbutyrophenone hydrochloride is substituted for 4-[4-[α-(p-tert-butylphenyl)-α-hydroxybenzyl]piperidino]butyrophenone hydrochloride and the reaction mixture is refluxed for three hours, α-(4-tert-butylphenyl)-4-(α-cyclohexyl-α-hydroxybenzyl)-1-piperidinebutanol is obtained, M.P. 75°–81°C. This compound was converted to the the hydrochloride salt, M.P. 240°–242.5°C. (dec.) by the usual methods.

EXAMPLE 3

4-[4-[α-(o-Anisyl)benzylidene]-α-(p-tert-butylphenyl)-1-piperidinebutanol]

To a mixture of 3 g (0.0075 mole) of 4-[4-[α-(oanisyl)-α-hydroxybenzylidene]piperidino]-4'-tert-butyl-butyrophenone in methanol is added excess potassium borohydride. The reaction mixture is refluxed for about 7 hours then evaporated. Water is poured onto the remaining solid which is then extracted with ether, dried over magnesium sulfate and filtered. The filtrate is concentrated to an oil which is allowed to remain in pentane overnight. The resulting solid material is recrystallized from acetone-hexane to give 4-[4-[α-(o-anisyl)benzylidene]-α(p-tert-butylphenyl)-1-piperidinebutanol], M.P. 97°–100°C.

EXAMPLE 4

4-[α-(p-tert-Butylphenyl)-α-hydroxybenzyl]-α-(p-tert-butylphenyl)-1-piperidinebutanol To 8.0 g (0.0143 mole) of 4-[4-[α-(p-tert-butylphenyl) α-hydroxybenzyl]piperidino]-4'-tert-butyl-butyrophenone hydrochloride dissolved in 50 ml of methanol is added with stirring a solution of 0.9 g (10% molar excess) of potassium hydroxide in methanol after which 1.54 g of potassium borohydride is added with stirring. The reaction mixture is allowed to react for about 3 hours at room temperature, after which the methanol is removed. Water is added to the remaining residue which is then extracted with ether, dried over magnesium sulfate, and filtered through celite. The filtrate is evaporated under vacuum, and the remaining solid is recrystallized several times from ethanol-water filtering while hot to give 4-[α-(p-tert-butylphenyl)-α-hydroxybenzyl]-α-(p-tert-butylphenyl)-1-piperidinebutanol, M.P. 179°–181.5°C.

EXAMPLE 5

When in the procedure of Example 4 an appropriate equivalent amount of the butyrophenone derivatives listed below are substituted for 4-[4-[α-(p-tert-butylphenyl)-α-hydroxybenzyl]piperidino]-4'-tert-butyl-butyrophenone hydrochloride the respective products listed below are obtained:

| Butyrophenone Derivative | Product |
| --- | --- |
| 4-[4-(α-hydroxy-α-phenylbenzyl)piperidino]-1-(2-naphthyl)-butan-1-one hydrochloride, M.P. 206.5–208.5°C. | 4-(α-hydroxy-α-phenylbenzyl)-α-(2-naphthyl)-1-piperidinebutanol |
| 4'-cyclopentyl-4-[4-(α-hydroxy-α-phenylbenzyl)-piperidino]butyrophenone hydrochloride, M.P. 232–234°C. | 4-(α-hydroxy-α-phenylbenzyl)-α-(p-cyclopentyl-phenyl)-1-piperidinebutanol |
| 4'-tert-butyl-4-[4-[α-hydroxy-α-(p-tolyl)-benzyl]piperidino]-butyrophenone hydrochloride, M.P. 194–196.5°C. | 4-[α-hydroxy-α-(p-tolyl)benzyl]-α-(p-tert-butylphenyl)-1-piperidinebutanol |
| 4-[4-(α-hydroxy-α-phenylbenzyl)piperidino]-4'-neopentylbutyrophenone hydrochloride, M.P. 227–229°C. | 4-(α-hydroxy-α-phenylbenzyl)-α-(p-neopentylphenyl)-1-piperidinebutanol |
| 4'-tert-butyl-4-[4-[α-hydroxy-α-(p-chlorophenyl)-benzyl]piperidino]butyrophenone hydrochloride, M.P. 238.5–240°C. | 4-[α-hydroxy-α-(p-chlorophenyl)benzyl]-α-(p-tert-butylphenyl)-1-piperidinebutanol |
| 4'-tert-butyl-4-[4-[α-(p-tolyl)benzylidene]-piperidino]butyrophenone hydrochloride, M.P. 187–189°C. | 4-[α-(p-tolyl)-benzylidene]-α-(p-tert-butylphenyl)-1-piperidinebutanol |

-continued

| Butyrophenone Derivative | Product |
|---|---|
| 4'-fluoro-4-[4-[α-hydroxy-α-(p-chloro-phenyl)benzyl]piperi-dino]butyrophenone hydrochloride. M.P M.P. 154°C. (dec.) | 4-[α-hydroxy-α-(p-chlorophenyl)benzyl]-α-(p-fluorophenyl)-1-piperidinebutanol |
| 4-[4-[α-hydroxy-α-(p-n-propylphenyl)benzyl]-piperidino]-1-(2-thienyl)-butan-1-one hydrochloride | 4-[α-hydroxy-α-(p-n-propylphenyl)benzyl]-α-(2-thienyl)-1-piperidinebutanol |
| 3-[4-[α-(p-n-butoxyphenyl)-α-hydroxybenzyl]piperi-dino]propiophenone hydrochloride | 4-[α-(p-n-butoxy-phenyl)-α-hydroxy-benzyl]-α-phenyl-1-piperidinepropanol |
| 2-[4-(α-hydroxy-α-phenylbenzyl)piperi-dino]-4'-n-pentoxy-acetophenone hydrochloride | 4-(α-hydroxy-α-phenylbenzyl)-α-(p-n-pentoxyphenyl)-1-piperidineethanol |
| 4-[4-[α-(p-bromo-phenyl)benzyl]piper-idino]-4'-methoxy-butyrophenone hydro-chloride | α-(p-anisyl)-4-[α-[p-bromophenyl)benzyl]-1-piperidinebutanol |
| 4'-cyclopropyl-4-[4-[α-(o-tolyl)benzyl]piperi-dino]butyrophenone hydrochloride | 4-[α-(o-tolyl)benzyl]-α-(p-cyclopropylphen-yl)-1-piperidine-butanol |
| 4-[4-[α-(p-ethylphenyl)-benzyl]piperidino]-4'-fluorobutyrophenone hydrochloride | 4-[α-(p-ethylphenyl)-benzyl]-α-(p-fluoro-phenyl)-1-piperi-dinebutanol |
| 4'-dimethylamino-4-[4-[α-hydroxy-α-(p-chloro-phenyl)benzyl]piperi-dino]butyrophenone hydrochloride | α-(p-dimethylamino-phenyl)-4-[α-hydroxy-α-(p-chlorophenyl)-benzyl]-1-piperidine-butanol |
| 4-[4-(diphenylmethylene)-piperidino]-1-(2-naph-thyl)butan-1-one hydro-chloride | 4-(diphenylmethyl-ene)-α-(2-naphthyl)-1-piperidinebutanol |
| 4-[4-(diphenylmethylene)-piperidino]-4'-neopentyl-butyrophenone hydrochloride | 4-(diphenylmethylene)-α-(p-neopentylphenyl)-1-piperidinebutanol |
| 4-[4-[α-(o-anisyl)benzyl-idene]piperidino-4'-tert-butylbutyrophenone hydrochloride | 4-[α-(o-anisyl)ben-zylidene]-α-(p-tert-butylphenyl)-1-piper-idine butanol |

The following examples are illustrative of pharmaceutical compositions containing as active ingredients compounds of this invention.

EXAMPLE 6

An illustrative composition for hard gelatin capsules is as follows:

| (a) | α-(4-tert-butylphenyl)-4-(α-cyclohexyl-α-hydroxybenzyl)-1-piperidinebutanol | 10 mg |
|---|---|---|
| (b) | talc | 5 mg |
| (c) | lactose | 100 mg |

The formulation is prepared by passing the dry powders of (a) to (c) through a fine mesh screen and mixing them well. The powder is then filled into hard gelatin capsules at a net fill of 115 mg per capsule.

EXAMPLE 7

An illustrative composition for tablets is as follows:

| (a) | 4-[4-[α-(o-anisyl)-benzylidene]-α-(p-tert-butyl-phenyl)-1-piperidinebutanol | 5 mg |
|---|---|---|
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 8

An illustrative composition for an aerosol solution is the following:

| | | Weight per cent |
|---|---|---|
| (a) | 4-[α-(p-tert-butylphenyl)-α-hydroxybenzyl)-α-(p-tert-butylphenyl)-1-piperidine-butanol | 5.0 |
| (b) | ethanol | 35.0 |
| (c) | dichlorodifluoromethane | 60.0 |

The materials (a), (b) and (c) are packaged in 15 ml stainless steel containers equipped with a metering valve designed to meter 0.2 grams per dose, an equivalent of 10 mg of novel compound (a).

EXAMPLE 9

An illustrative composition for an aerosol suspension is the following:

| | | Weight per cent |
|---|---|---|
| (a) | 4-(α-hydroxy-α-phenylbenzyl)-α-(p-cyclopentylphenyl)-1-piperidinebutanol (particle size <10μ) | 20.0 |
| (b) | sorbitan trioleate | 0.5 |
| (c) | dichlorodifluoromethane | 39.75 |
| (d) | dichlorodifluoroethane | 39.75 |

The materials (a) – (d) are packaged in 15 ml stainless steel containers equipped with a metering valve designed to meter 50 mg per dose, an equivalent of 10 mg of novel compound (a).

EXAMPLE 10

An illustrative composition for an injectable suspension is the following 1 ml ampul for an intramuscular injection.

| | | Weight per cent |
|---|---|---|
| (a) | 4-[α-(p-tolyl)benzylidene]-α-(p-tert-butylphenyl)-1-piperidinebutanol (partical size <10μ) | 1.0 |
| (b) | polyvinylpyrrolidone (M.W. 25000) | 0.5 |
| (c) | lecithin | 0.25 |
| (d) | water for injection to make | 100.0 |

The materials (a) to (d) are mixed, homogenized, and filled into 1 ml ampuls which are sealed and autoclaved 20 minutes at 121°C. Each ampul contains 10 mg per ml of novel compound (a).

The optical isomers of the compounds of this invention may be separated by using a (+) or (–) binaphthylphosphoric acid derivative or a salt of said derivative and an assymetric base by the method described by R. Viterbo et al., in Tetrahedron Letters No. 48, pp. 4617–4620 (1971).

We claim:

1. A compound selected from a base of the formula wherein R¹ is selected from the group consisting of cyclohexyl, phenyl or a substituted phenyl ring wherein the substituent on the substituted phenyl ring is attached at the ortho, meta, or para position of the phenyl ring and is selected from the group consisting of halogen, a straight or branched lower alkyl group of from 1 to 4 carbon atoms, or a lower alkoxy group of from 1 to 4 carbon atoms; $R^2$ is selected from hydrogen or hydroxy; $R^3$ is hydrogen; or $R^2$ and $R^3$ taken together form a second bond between the carbon atoms bearing $R^2$ and $R^3$; n is an integer of from 1 to 3; Z is selected from the group consisting of thienyl, naphthyl, phenyl or a substituted phenyl ring wherein the substituent on the substituted phenyl ring is attached at the ortho, meta, or para position of the phenyl ring and is selected from the group consisting of halogen, a straight or branched alkyl group of from 1 to 6 carbon atoms, an alkoxy group of from 1 to 6 carbon atoms, a cycloalkyl group of from 3 to 6 carbon atoms, di(lower)alkylamino, or a saturated monocyclic heterocyclic group such as pyrrolidino, piperidino, morpholino or N-(lower)alkylpiperazino with the proviso that when R¹ is phenyl, Z is naphthyl or a substituted phenyl ring wherein the substituent on the substituted phenyl ring is attached at the ortho, meta of para position of the phenyl ring and is selected from the group consisting of a straight or branched alkyl group of 5 or 6 carbon atoms, an alkoxy group of 5 to 6 carbon atoms, of cycloalkyl of 3 to 6 carbon atoms; and pharmaceutically acceptable acid addition salts thereof.

2. A compound of claim 1 wherein R¹ is cyclohexyl.

3. A compound of claim 2 which is α-(4-tert-butylphenyl)-4-(α-cyclohexyl-α-hydroxybenzyl)-1-piperidinebutanol or a pharmaceutically acceptable acid addition salt thereof.

4. A compound of claim 1 wherein R¹ is a substituted phenyl ring.

5. A compound of claim 4 which is 4-[α-(o-anisyl)-benzylidene]-α-(p-tert-butylphenyl)-1-piperidinebutanol or a pharmaceutically acceptable acid addition salt thereof.

6. A compound of claim 1 wherein R¹ is phenyl.

7. A compound of claim 4 which is 4-[α-(p-tolyl)benzylidene]α-(p-tert-butylphenyl)-1-piperidinebutanol or a pharmaceutically acceptable acid addition salt thereof.

* * * * *